United States Patent [19]
McFarlane

[11] Patent Number: 4,877,394
[45] Date of Patent: Oct. 31, 1989

[54] APPARATUS FOR MOLDING PARTS HAVING SMALL DIAMETER HOLE

[75] Inventor: Richard H. McFarlane, Geneva, Ill.

[73] Assignee: Taut Inc., Geneva, Ill.

[21] Appl. No.: 496,894

[22] Filed: May 23, 1983

Related U.S. Application Data

[62] Division of Ser. No. 302,490, Sep. 16, 1981, abandoned.

[51] Int. Cl.⁴ .................. B29C 45/03; B29C 45/27
[52] U.S. Cl. ................................ 425/567; 249/63; 249/151; 249/177; 264/154; 264/328.1; 264/328.12; 264/313; 425/466; 425/577
[58] Field of Search ............. 425/111, 466, 577, 567; 264/154, 328.1, 313, 328.12; 249/63, 151, 177

[56] References Cited
U.S. PATENT DOCUMENTS

| 2,886,875 | 5/1959 | Anderson | 425/111 |
| 3,385,553 | 5/1968 | Braun | 425/577 X |
| 3,724,982 | 4/1973 | Davis | 425/111 |
| 4,005,166 | 1/1977 | Quick | 264/154 |

Primary Examiner—Jan H. Silbaugh
Assistant Examiner—Leo B. Tentoni
Attorney, Agent, or Firm—John Cyril Malloy

[57] ABSTRACT

A process for applying tension to the extending ends of a thin wire core of a mold to apply tension to the core during the molding process to maintain alignment of the core at all times during the molding process. Also included is apparatus for carrying out the process. Also included is a generally tubular part having a fine diameter hole therethrough.

7 Claims, 1 Drawing Sheet

APPARATUS FOR MOLDING PARTS HAVING SMALL DIAMETER HOLE

This is a divisional application of my copending patent application Ser. No. 302,490 filed Sept. 16, 1981, now abandoned.

BACKGROUND OF THE INVENTION

In the past it has often been desired to mold plastic parts with a straight, relatively small diameter hole through it. An example is a medical catheter in the form of a jacket or sleeve of plastic material through which a medical needle is to be inserted. If the hole is not of constant diameter or is somewhat misaligned, upon insertion of the needle into coaxial relation within the plastic sleeve or jacket, the tip of the needle may pierce the side wall or shave some of the material from it which results in a combination which is not usable. For example, if some small plastic shavings enter the needle, it cannot be used for injection into the arm of a patient because the shavings would enter the blood. There are numerous other stiuations in which a relatively fine hole is required through a tubular plastic molded part, whether the fine hole is coaxial with the part or not, or whether the part is cylindrical or not; and generally the term tubular as used herein refers to parts which have at least one fine through hole. Oftentimes such molded plastic parts are required to be of a thin wall of constant thickness with a longitudinally extending fine hole through it. In the past, when the plastic is flowed into a cavity about a fine core, that is a core of small diameter, the pressure under which the plastic must be held in order to flow through the runner and into the cavity during the molding operation, tends to cause a thin mold core to wander from perfect or near perfect axial alignment rendering a defective part. For this reason, the prior art has been limited to relatively short tubular lengths in relation to the diameter of the hole through it. If for example the tube is to be relatively long, a small hole, especially a small hole in a thin walled tube is difficult or impossible to make. Different materials provide different problems. For example, polyurethane plastic material is somewhat difficult to mold into a thin walled plastic molded part with a fine diameter hole axially through it. Similarly, problems occur in molding thin walled plastic parts with a fine diameter hole through it which are not of rigid plastic but, rather, a relatively bendable plastic material such as is used in catheters for medical devices. The same is true of polypropylene materials as well as the commercially available plastic material known as Teflon manufactured by and made available commercially by the E. I. duPont de Nemenours Company. For example, it is often required to make small diameter holes of about 0.020 inches in a tube of plastic of about an inch or more in length with an outside diameter of about 0.032 inch so that the wall is relatively thin and in the range of about 0.006 inch in thickness. Oftentimes it is desired that the hole or passageway through the molded plastic part be about 0.002 inch to about 0.100 inch in diameter. The difficulty has been that the core is relatively fine in such molding operations as a necessity and it will not stay centered within the cavity of the mold when the mold closes and is under pressure.

In the past, some plastic parts have been made which have small holes through them. This has been done by drilling with a fine drill or by a laser beam and the length of the tube with the fine hole is of a limited length. Also it is known to extrude a tube and draw it to a smaller diameter. The former presents limitations as to the thickness requirement of the tube wall and the latter is limited to a hole which is cylindrical, that is, it cannot be internally stepped for example. Generally such prior art devices would not be practical in quantities in a production setting.

The present invention provides a process generally for molding a relatively long generally tubular plastic piece; usually with a thin wall, and having a relatively small diameter axial hole through it, which may not be necessarily cylindrical, e.g., it may be stepped; and the process consists of positioning mating mold parts about a thin wire core to define a mold having an annular cavity about the wire and a runner means to flow plastic into the mold cavity and includes the step of maintaining the mold parts in mold defining relation about a relatively thin wire which extends from the mold and through the cavity which wire is subjected to tension while simultaneously flowable plastic is injected into the cavity through the runner and coaxially about the wire while it is under tension.

OBJECTS OF THIS INVENTION

It is an object of this invention to provide a process for molding relatively small diameter tubular members usually of thin wall and a product of the process comprising a thin walled plastic tube which has been molded and which defines a relatively thin or fine passageway through the molded plastic part.

In accordance with this object and other objects which will become apparent, including the provision of a process as well as a product of the process, the following invention will now be described with reference to the accompanying drawings in which:

DESCRIPTION OF THE PREFERRED EMBODIMENT

Figure 1:
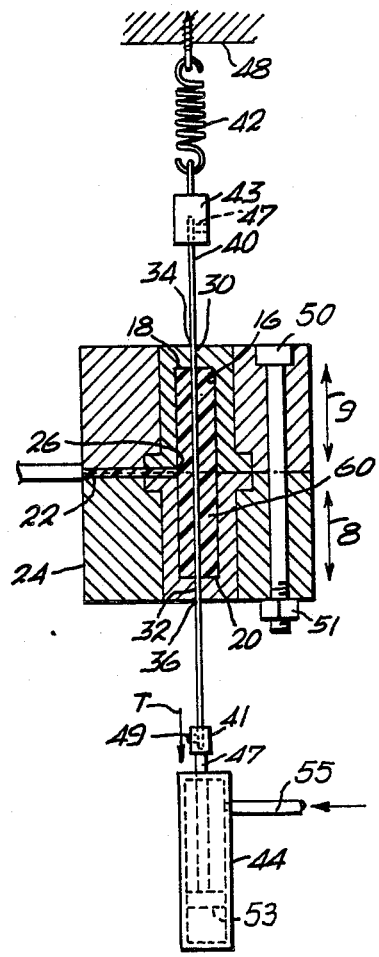
FIG. 1 is a view in cross section illustrating one embodiment of the instant invention.

Referring to FIG. 1, there is shown a first mold part and a second mold part which are movable in the direction of the arrows 8 and 9 into and out of mold relationship. These mold parts, when in mold relationship, define a cavity 16 having an upper end 18 and a lower end 20 as well as a runner 22 extending from the exterior surface 24 of the mold to a gate 26 into the cavity. Additionally, the mold defines passageways 30 and 32 which extend from the cavity exteriorly of the mold upwardly and downwardly a at 34 and 36. A thin wire core designated by the numeral 40 extends through these passageways and the cavity and has a portion exteriorly of the mold at each end. To the exteriorly accessible portions of the wire, usually the ends of this thin wire core, tension is applied by a suitable tensioning means, such as 42 and 44. It will be apparent that one end might be secured to a clamping device 43, and if desired, connected by the spring means or directly to a fixed station 48 so that a piston 47 with a clamp means 41 may be utilized to apply tension in the direction of the arrowed line T. The clamping device 43 and, in the piston end, the clamp means 41 may be in the form of a recess in which a wire end is received and held by a set screw such as 47 and 49, for example.

In operation, a tubular piece 60 is molded within the cavity 16 of the mold and about the wire as plastic is injected into the mold while the mold parts are maintained in mold defining relation by suitable means such as that designated by the clamp means or screw and nut 50 and 51.

Figure 2:
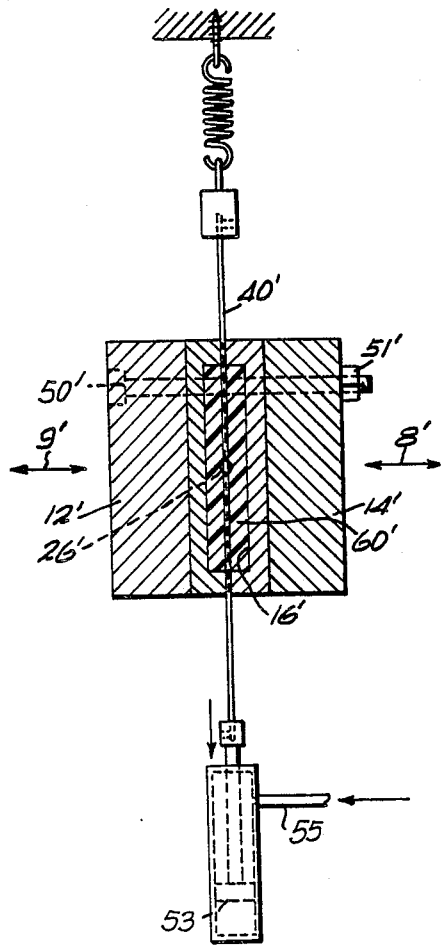
FIG. 2 is a view in cross section illustrating an alternative embodiment of the instant invention.

It will be appreciated that while the mold parts in FIG. 1 are annularly arranged in mating relation with one another about the wire core 40, the mold parts may be as shown in FIG. 2. In FIG. 2 the mold parts are of the type which define a vertical part line and are movable in the direction of the arrowed lines 8' and 9'. In this embodiment the clamp means 50' and 51' maintain the two mold parts in mold closing relation yet in a somewhat different attitude, see FIG. 2. The parts are not here redesignated except that the mold parts are designated by the numerals 12' and 14' about the cavity 16' through which plastic is injected through the gate 26' to define a cavity about the wire core 40' to make the plastic piece 60'.

The equipment used in the process is conventional, such as clamps, springs, presses, mold parts, and a hydraulic piston means to maintain predetermined tension upon the wire. The piston cylinder 53 is provided with a connection to a gas or liquid source through a supply tube 55 and a valve, not shown, may be used to regulate the applied tension.

In a preferred embodiment a hole of about 0.013" diameter is created in a molded plastic part by utilizing a fine wire core to which there is applied about 30 pounds of tension and which hole may be relatively long about 1", and wherein the wall is of a thickness of about 0.004" to 0.006". Under the injection pressure a thin core pin would shift, but in this embodiment the problem is overcome by applying this tension which stiffens the core tending to maintain it in a straight line and in response to any pressures exerted upon it urging back into a straight line tending to maintain it in a stiffened and straight path at all times between the passageways and in spanning relation of the cavity.

The material of the plastic part may be polypropylene, Teflon, polyurethane, or polyethylene which may be used in combination with barium sulfate to make it radio opaque. The product for example, may be utilized in the medical field for making catheters and the like, which should not be stiff and hence should be of a thin walled construction. Moreover, the thickness of the wall throughout its length should be substantially uniform, so that, upon bending, the molded part or tubular length will define a fair curve instead of buckling at a weakened thin wall zone which would tend to or actually occlude the passageway through it, which would be deliterious in use.

During the injection process, there may be some tendency of the wire core pin to shift or respond to the pressure of the inflow of plastic; however, by the reason of the tension it is believed to be maintained in such a fashion as to always wander or drift back to a straight line notwithstanding any tendency to wander during the actual injection process. This process avoids the prior art techniques of preparing plastic parts with fine holes such as the extrusion technique which requires that the extruded length be drawn down in order to achieve a thin walled tube with a fine diameter. This process provides for a molding of the part with the fine hole through it and in those instances where a thin wall is also required, a thin walled tubular section with a fine hole through it. In the preferred embodiment the core pin of wire may be between about 0.002 inch to about 0.100 inch in diameter and in utilizing the process, the fine wire is maintained centered by the tension when the mold closes and the plastic is being injected. While the plastic is being injected, the two-piece mold is held in mold defining relation and an air cylinder may be utilized with the piston type gripper means described above to apply tension to the wire. The tension of the wire core is not beyond the elastic limit of the wire and usually about 40 pounds per square inch or less and preferably about 35 pounds per square inch so that the wire is in equilibrium and under tension which is not sufficient to distort it. Of course the tension will vary depending upon the diameter of the wire or, expressed otherwise, the diameter of the hole to be located in the molded part, for example, if the hole is to be 0.002, the tension will be a few psi while if it is to be 0.100 inches then substantially more pounds per square inch of tension may be applied. In use, the temperature of the platic during the molding process is maintained at a heat of about 300°–500° F. so that the plastic flows relatively freely through the runners and into and about the cavity to make the molded piece. Generally the operating pressure of such presses is about 5 to 10,000 pounds per square inch. The passageways through which the wire mold extend are described as snugly fitting the wire, that is within the techniques well known in the art, sufficient so that there will be some slippage possible in order to transmit the tension to the cavity but small enough so that there will not be flash created. In the art about 0.001 inch opening is known to be satisfactory for this purpose. Thus there is described a process for making a relatively fine straight hole of constant diameter to provide a molded plastic piece of uniform wall thickness and which may be of thin wall constructions. The preferred temperature range for operating is about 400° F.; however, it will be appreciated by those in the art that when Teflon is utilized the temperature is elevated somewhat to about 700° F. The material of the wire core is preferably a strong stainless steel hardened spring wire. The tension as pointed out above will vary depending upon the diameter of the wire core with as much tension being applied as possible preferably so that it does not break or elongate, in other words, the effort is made to apply tension relatively close to but not greater than the tensile strength and to provide a stiff wire spanning the cavity which will tend to maintain a straight line and always urge itself into that orientation as the flowable plastic begins to set about it and prior to its actually solidifying. When the plastic has solidified, the mold is opened, the tension on the wire is released, and the part may be removed by moving it down the wire to a free end. As is conventional the mold plate is ordinarily of a soft material relatively speaking and includes a hardened steel insert, which is also conventional. These are provided in both mold parts but the designations are not here repeated.

Figure 3:
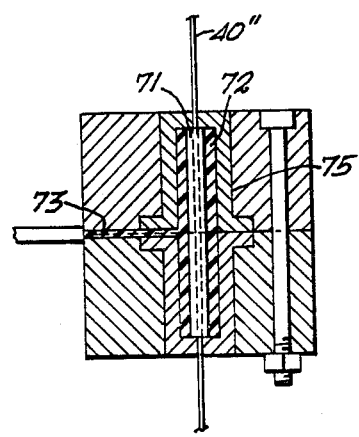
FIG. 3 is an alternative embodiment of the instant invention.

Referring to FIG. 3, it will be apparent that, if desired, about the wire core 40" a sleeve 71 may be positioned and thereafter an outer plastic layer 72 may be injected through the runner 73 into the cavity 75.

Figure 4:
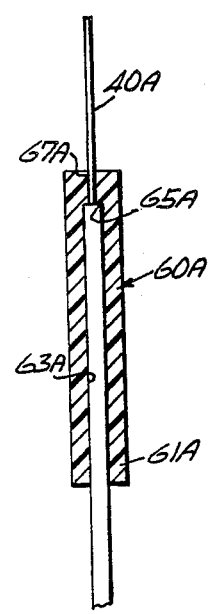
FIG. 4 illustrates a product made by the process.

Referring to FIG. 4, the wire is designated by the numeral 40A and a molded plastic part 60A is illustrated which is intended to be of a thin walled molded form as designated by the numeral 61A. It will be noted that the hole through the device 63A is a fine hole, that is, small in diameter and, additionally, it is stepped as at 65A defining a shoulder and a somewhat smaller hole 67A. One of the advantages of the flexibility provided in manufacturing techniques by utilizing this process will be apparent to those skilled in the art wherein it is seen that the interior of the molded plastic thin walled part with the fine hole through it may be stepped, a product which is not possible by an extrusion process, since by its nature an extrusion calls for and requires a uniform cross section throughout the length of the product.

While the instant invention has been shown and described herein in what is conceived to be the most practical and preferred embodiments, it is recognized that departures may be made therefrom within the scope of the invention, which is therefore not to be limited to the details discloed herein but is to be accorded the full scope of the claims so as to embrace any and all equivalent apparatus and articles.

What is claimed is:

1. An apparatus for molding a long tubular plastic piece of thin wall thickness which includes a central coaxial hole extending therethrough along the length thereof, said apparatus comprising:
    (a) a mold comprising a first and a second mating mold part positionable into mating engagement with one another and structured when so positioned to define a mold cavity within said mold,
    (b) said mold cavity having an interior longitudinal dimension between opposite ends thereof substantially equal to the length of the resulting plastic piece,
    (c) said mold including a passageway having a predetermined transverse dimension located at each of said opposite ends of said mold cavity and in communicating relation between said mold cavity and the exterior of said mold,
    (d) each passageway disposed in coaxial relation with one another and with a central longitudinal axis of said mold cavity,
    (e) a wire core including an intermediate portion disposed within said mold cavity and extending the length thereof and in coaxial relation to said mold cavity,
    (f) said wire core including a first end and a second end extending from said intermediate portion, each of said ends disposed to pass through one of said passageways and extend outwardly from said mold cavity so as to be exteriorly accessible relative thereto,
    (g) tension applying means for tensioning said wire core and located in spaced relation to and exteriorly of said mold and including a first tensioning means and a second tensioning means secured to said first exteriorly accessible end of said core and said second exteriorly accessible end of said core respectively for applying tension thereto,
    (h) said first tensioning means anchored in place and structured to maintain and resist any force applied to said wire core, said second tensioning means structured to selectively apply an adjustable axially directed tensioning force to said second exteriorly accessible end and against said first tensioning means,
    (i) plastic injection means mounted at least in part on said mold and in communicating relation with said mold cavity, said plastic injection means structured and disposed for directing flowable plastic material into said cavity and about said wire core,
    (j) said second tensioning means adapted to subsequently adjust axial force applied to said second exteriorly accessible end to compensate for distorting pressures on said wire core subsequent to the injection of plastic material within said cavity, and
    (k) said wire core disposed and maintained in a straight line coaxial orientation relative to said mold cavity during molding formation of the plastic material into said plastic piece.

2. The device as set forth in claim 1 wherein said mold parts define a part line generally parallel to the wire core.

3. An apparatus as in claim 1 wherein said first tensioning means comprises biasing means secured to said first exteriorly accessible end of said wire core, whereby deviations in tension on said wire core are compensated for.

4. An apparatus as in claim 3 wherein said second tensioning means comprises a fluid actuated piston and cylinder assembly secured to said second exteriorly accessible end so as to selectively exert adjustable and axially directed tensioning force thereon.

5. An apparatus as in claim 1 wherein said plastic injection means is disposed substantially laterally of said mold and including runner means disposed to inject flowable plastic material substantially transverse to said mold cavity and coaxially disposed wire core whereby the flowable plastic material fills said mold cavity in surrounding relation to said wire core.

6. An apparatus as in claim 1 wherein said predetermined transverse dimension of each passageway is of sufficient dimension to allow passage therethrough of respective first and second exteriorly accessible ends and blockage therethrough of any plastic material from within said mold cavity.

7. An apparatus as in claim 1 further comprising sleeve means disposed within said mold cavity in surrounding coaxial relation to said wire core, said sleeve means including a common transverse dimension along its length being greater than the transverse dimension of said wire core, said sleeve means extending along at least a portion of the length of said wire core, said plastic injection means and said sleeve means relatively disposed and structured to surround said sleeve means and any length of said wire core not covered by said sleeve means with flowable plastic material, whereby said central coaxial hole extending through said plastic piece has a stepped configuration.

* * * * *